Figure 1:
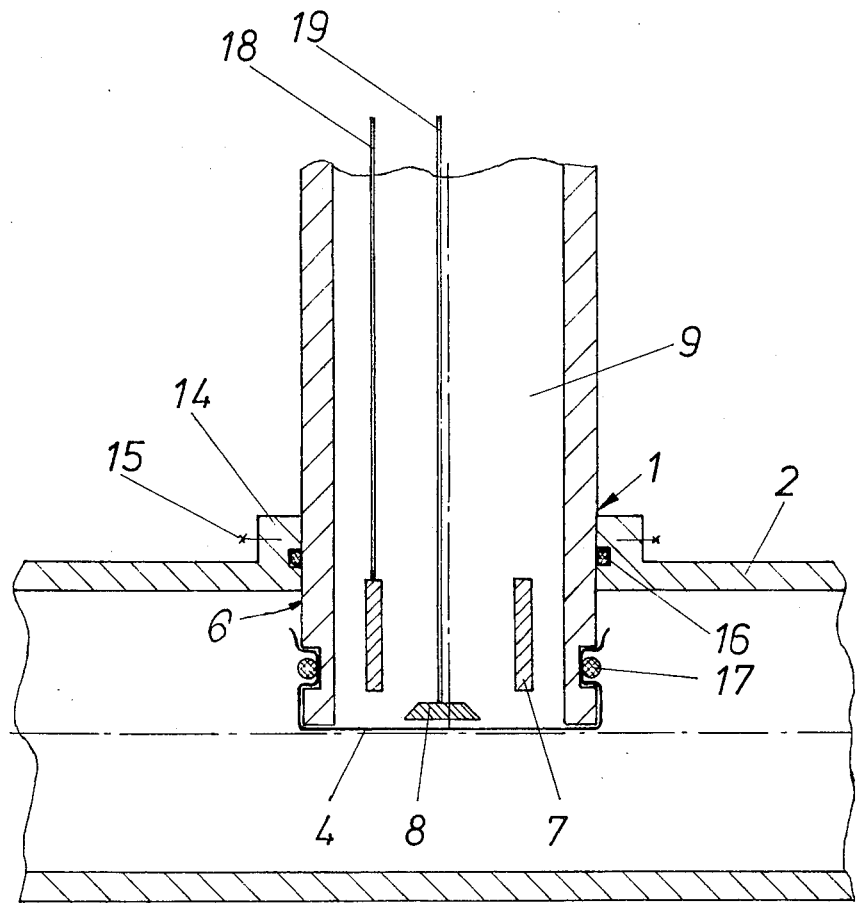

United States Patent [19]
Gamer et al.

[11] 3,988,233
[45] Oct. 26, 1976

[54] APPARATUS FOR MEASURING DISSOLVED GASES IN A FLUID MEDIUM

[75] Inventors: Gerold Gamer; Gangolf Bräunlich, both of Heidelberg, Germany

[73] Assignee: BBC Brown Boveri & Company Limited, Baden, Switzerland

[22] Filed: May 7, 1975

[21] Appl. No.: 575,152

Related U.S. Application Data
[63] Continuation of Ser. No. 429,855, Jan. 2, 1974, abandoned.

[30] Foreign Application Priority Data
Jan. 5, 1973  Germany............................ 2300417

[52] U.S. Cl............................................... 204/195 P
[51] Int. Cl.² ......................................... G01N 27/46
[58] Field of Search ................. 204/1 P, 1 K, 195 P; 137/2, 93

[56] References Cited
UNITED STATES PATENTS
3,526,577  9/1970  Molloy ............................... 204/1 P FOREIGN PATENTS OR APPLICATIONS
726,863  2/1966  Canada............................ 204/195 P Primary Examiner—G. L. Kaplan
Attorney, Agent, or Firm—Pierce, Scheffler & Parker

[57] ABSTRACT

Apparatus for measuring dissolved gases in a fluid medium includes a tubular member which is inserted in a pipe line through which the fluid medium flows. This tubular member thus becomes a part of the pipe line and a portion of the inner wall surface thereof serves as a membrane through which the gas to be measured diffuses into a polarographic measuring cell which surrounds the tubular member and includes an annular electrolyte chamber and cathode and anode electrodes therein.

6 Claims, 10 Drawing Figures

APPARATUS FOR MEASURING DISSOLVED GASES IN A FLUID MEDIUM

This is a continuation of application Ser. No. 429,855 filed on Jan. 2, 1974, now abandoned.

The present invention relates to an improvement in the construction of apparatus for the measurement of dissolved gases in liquids or other gases flowing in a pipe line, and especially for dissolved oxygen in water, the device consisting principally of a gas-permeable membrane covering the entrance to a polarographic measuring cell and which contains spaced anode and cathode components and an electrolyte, the cell with its covering membrane being inserted into the pipe line in such manner that dissolved oxygen in water flowing through the pipe line, for example, permeates the membrane and enters into the cell.

The function of such measuring cell, and the requirements to be met by its components, for example, in connection with $O_2$, are as follows: The membrane should be well permeable with respect to oxygen, but impermeable to impurities or surface-active and electro-active materials, and also to the electrolytic solution of the cell as well as to water.

The electrodes have the following function: At the cathode there are converted water and molecular oxygen into $OH^-$-ions, and at the anode there are produced the corresponding number of positive charge carriers. The potential for the electro-chemical conversion of the $O_2$-molecules originates either from the galvanic voltage of the cell proper or from an externally applied voltage. The flow of ions serves to measure the oxygen, diffused in through the membrane. The electrolyte takes part in the anode reaction and is consumed in unison with the anode.

The general object of the present invention is to provide an improved construction for the measuring cell which is installable in the pipe line system but without interfering in any manner with the flow of the fluid containing the dissolved gas desired to be measured through the pipe. This objective is attained in that the gas-permeable membrane component of the cell forms at least a part of the wall of a tubular member open at both ends and which is inserted into and actually becomes a part of the pipe line itself, the remainder of the cell structure including the spaced electrodes, i.e. cathode and anode positioned within a chambered portion containing the electrolyte being located in a radially outward direction from the membrane. Preferably the membrane extends completely around the inner periphery of the tubular member and the electrodes likewise extend completely around the membrane within the like extending electrolyte filled chamber so that the oxygen or other dissolved gas in the flowing liquid or other medium is provided with a maximum area for permeation into the cell chamber. The electrodes extending completely around the membrane can thus be formed by a helically coiled wire, or by a cylindrical grid, or by a perforated tube, or by rings. It is also possible to establish the required electrode components by means of a coating either directly at the membrane or at a sheath member constituting the radially outer wall of the cell chamber, or at a plastic carrier material.

One embodiment of the improved measuring cell which has proved its merits by practical tests, is characterized by the feature that the cathode covers only one portion of the cylindrical membrane, i.e. the area of the membrane is substantially greater than the area of the cathode, an arrangement which improves greatly the outflow of the hydroxyl ions. It was found that in the case of this design the use of a lead anode and a silver cathode was particularly advantageous. The galvanically generated polarization voltage makes feasible a low-cost construction and operation of such cell. Also, the anode can be increased in size, thus allowing operation at higher current intensity.

The reduction of the oxygen can be expressed generally by the following formula:

$$O_2 + 2 H_2O + 4 e^- \rightarrow 4 OH^-.$$

The secondary reaction of the OH ions with electrolyte and anode is determined by the electrolyte-electrode system. For example:

| Anode | Cathode | Electrolyte | Voltage | Reaction |
|-------|---------|-------------|---------|----------|
| Ag | Au | KCL | impressed | $4OH^- + 4KCl + 4Ag - 4e^- \rightarrow 4AgCl + 4KOH$ |
| Pb | Ag | KOH | galvanic | $4OH^- + 2Pb - 4e^- \rightarrow 2Pb(OH)_2$ |
| Pb | Ag | $KHCO_3$ | galvanic | $4OH^- + KHCO_3 + 2Pb - 4e^- \rightarrow 2Pb(HCO_3)_2 + 4KOH$ Reversion of electrolyte by dissolved $CO_2$: $KOH + CO_2 \rightarrow KHCO_3$ |

It will be advantageous to design all components in tubular or annular form.

The outer sheath of the measuring cell is made, for example, from a material which can be pierced by an injection syringe for the insertion of the electrolyte or it can be provided with fill holes. The sheath is also preferably flexible so as to facilitate pressure compensation. The sheath is fastened in place in known manner such as by tension rings, bolting or similar mounting devices, with sealing means inserted if necessary. The outer side of the measuring device is closed off gas-tight, and various means such as plastic coatings, varnishes and the like can be used for this purpose.

In a further improvement of the measuring cell there is provided between the cathode and the anode a support which can be penetrated by the electrolyte. This support is made most advantageously by a plastic in the form of a grid. If it is desired to omit such support, the cathode and/or the anode are constructed in the form of a coating at the membrane, or sheath respectively.

As a further improvement the membrane made of material that is permeable to gas is provided at its internal diameter with a diffusion-controlling layer. This has the advantage that a very brief time constant can be attained because the layer, possessing low permeability can be kept very thin.

Another improvement of the measuring cell is the subdivision of the space between the cathode and the anode into several individual chambers by dividing walls, either axially or radially. Such arrangement provides parallel operation of several cells and offers the following advantages over a single cell:

1. Low current load per cell, resulting in greater durability;
2. Stronger total current in comparison with a single cell, thus facilitating the processing of signals;
3. The current distribution will be more uniform in comparison with single cells of identical current intensity, and lesser drift phenomena due to aging can be expected;
4. Low incidence of failures because in a case of n-cells, the variation by one cell, for example, caused by local fluctuations of the membrane, represents only 1 : n of the total variation;
5. Increase in the usable membrane area, resulting in a more uniform diffusion current.

Figure 2:
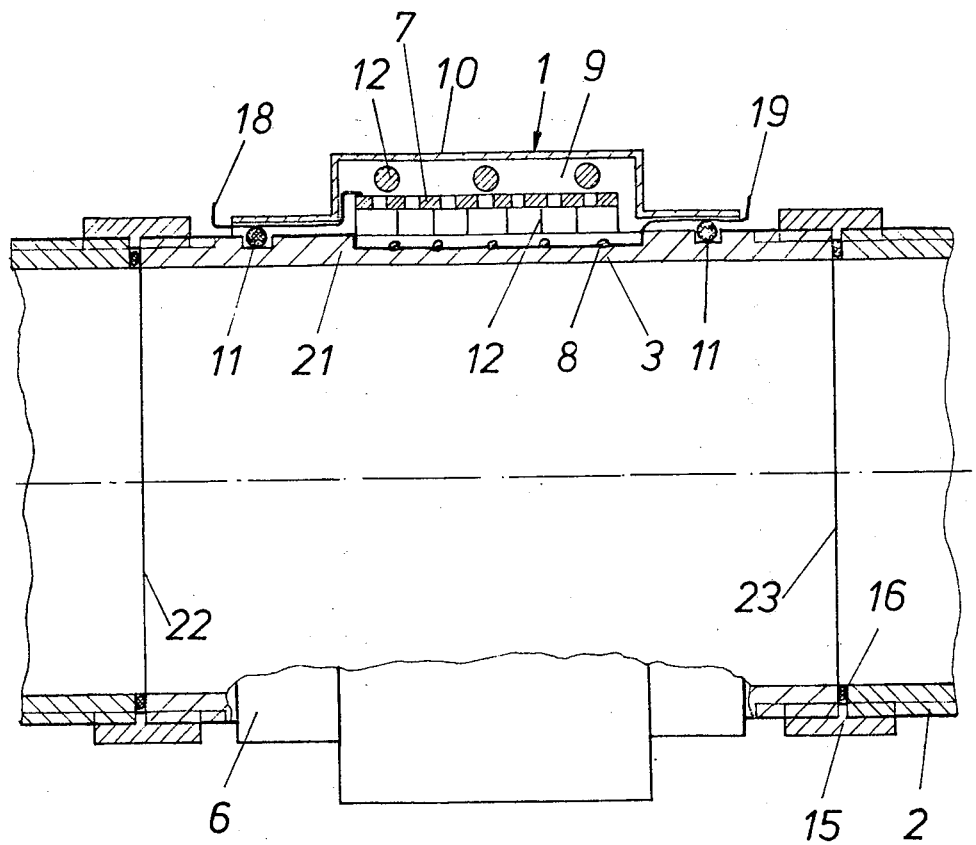

The foregoing as well as other objects and advantages inherent in the improved polarographic measuring cell structure for dissolved gases will become more apparent from the following detailed description of several different embodiments thereof and from the accompanying drawings wherein:

FIG. 1 is a central sectional view through a known measuring cell structure mounted in a pipe line and which has been included for the purpose of comparison with the improvement thereover in accordance with the present invention;

FIG. 2 is a similar sectional view of one embodiment of the measuring cell structure in accordance with the invention; and FIGS. 3 to 10 are similar sectional views which illustrate various modifications of the structure shown in FIG. 2, all of them having in common a tubular member open at both ends for insertion into a pipe line, a gas-permeable membrane extending completely around the inner periphery of this tubular member, the electrodes surrounding the membrane in the electrolyte-filled chamber and the latter being closed off by a sheath.

In all of the views, those components having the same function have been assigned the same identifying reference numerals even though they may differ somewhat in actual structure.

With reference now to FIG. 1, a typical known design in accordance with the prior art for measuring $O_2$ comprises a polarographic measuring cell 1 including a tubular vessel 6 which is inserted through a flanged opening 14 into a pipe line 2 through which flows the liquid containing the dissolved gas to be measured, a seal ring 16 being provided at the opening to prevent leakage of fluid from the pipe. A screw or other equivalent connection 15 at the flange 14 serves to fix the end portion of the tubular vessel 6 in the desired position within the pipe line and this is somewhat difficult since the flange is required to be designed in conformity with the shape of the vessel. A further disadvantage is that the gas-permeable membrane 4 is stretched across the lower end of the tubular vessel 6 within the pipe line 2 without additional support. Since a retaining ring 17 seated in a peripheral groove provided in the wall of the tubular vessel serves to stretch the membrane over the end there is a potential danger of defects in the tautness of the membrane which may be caused either during installation or after a relatively short time in operation. Furthermore, this type of construction for the measuring device is subject to extreme fouling as well as damage by any viscous materials present in the liquid or other medium conveyed through the pipe line. The anode structure is identified by numeral 7 and the cathode by 8, and the leads for the anode and cathodes are designated by 18 and 19. The electrolyte filled chamber inside the vessel is designated 9.

Comparison of FIG. 1 with FIG. 2 which illustrates one embodiment of the improved construction of the measuring device in accordance with the present invention will readily reveal its advantages over prior known constructions as has been represented by FIG. 1. The "vessel" part of cell 1 indicated generally by numeral 6 comprising a tubular member 21 open at both ends 22, 23 and which has an inner diameter equal to that of the pipe line 2 is inserted into the line by means of coupling sleeves 15 overlapping the abutting ends of the tubular member and the corresponding ends of the pipe line, sealing rings 16 being provided at the joints to prevent leakage from the pipe line. The wall of the central portion of the tubular member 21 is reduced in diameter so as to provide a relatively thin wall portion 3 that functions as the membrane component of the cell. Accordingly the tubular member is made of such material as will enable the dissolved gaseous component in the liquid or other fluid passing through the pipe line to diffuse into the electrolyte filled chamber 9 but is impermeable with respect to the fluid in pipe line 2 and the electrolyte. Suitable materials usable for this purpose are ceramics, solid Teflon, metallic grids in Teflon, and sintered bodies with ceramics or metals. The cathode 8 is made in the form of a helical wire winding e.g. of silver surrounding and in contact with the thin-walled membrane serving portion 3 of the tubular member 21, and the anode 7 is depicted in the form of a cylindrical perforated sheet metal e.g. of lead of larger diameter than cathode 8 and spaced radially outwardly therefrom by means of a cylindrical support structure 12 permeable to the electrolyte. However, the electrode structures may take other forms such as a grid or ring and can be made from sintered metal, oxygeneous semiconductive material or porous carbon. Dimensioning of the electrodes should be selected carefully in order to avoid any excessive battery effect.

The measuring cell is completed by a sheath 10 which surrounds the tubular member 21. The end portions of this sheath are fitted to the end portions of the tubular member 21 by means including sealing rings 11 and the central portion of the sheath is of larger diameter so as to accommodate the anode 7 and its support structure 12 and establish the necessary wall structure for the electrolyte chamber 9. A lead-in 18 for the anode is passed through an axial passageway at one end of the sheath, and a similar lead-in 19 and passageway for the cathode is provided at the opposite end of the sheath.

Figure 3:
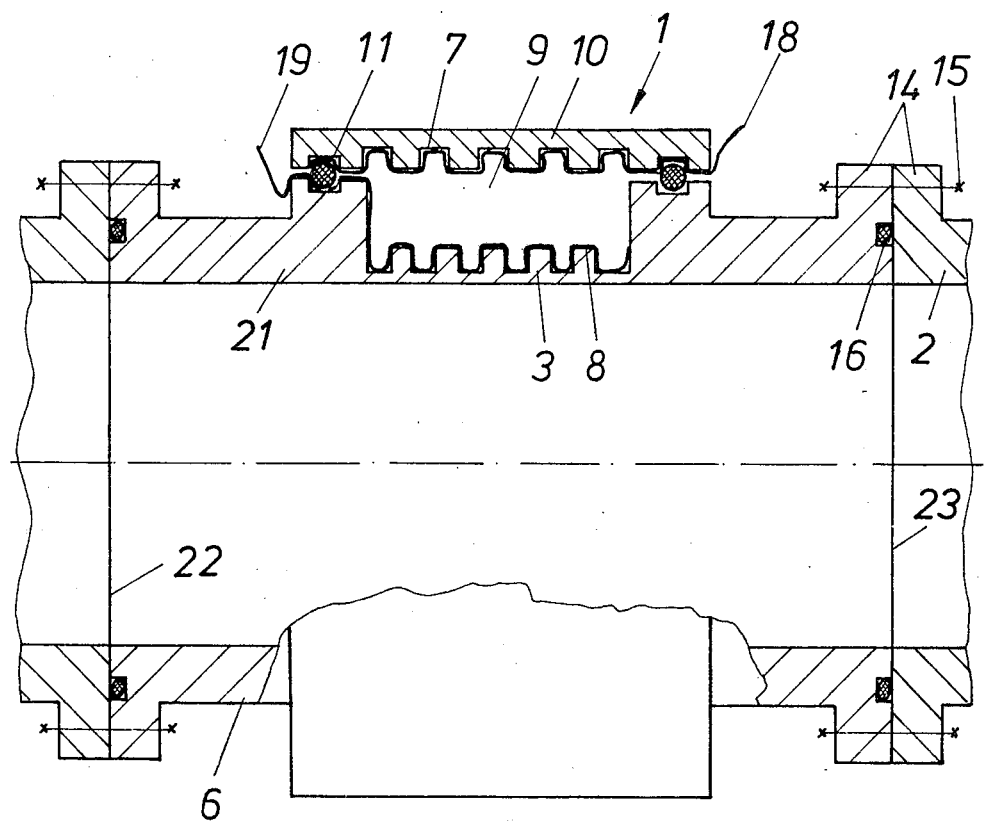

The embodiment illustrated in FIG. 3 is similar to that of FIG. 2 and those components corresponding to like functioning components of FIG. 2 have been accordingly identified by the same numerals. Differences are that the tubular member 21 is fitted into the pipe line 2 by means of abutting flanges 14 on these parts which are connected together by means of circumferentially spaced screws or bolts 15 and sealing rings 16. As in FIG. 2 tubular member 21 is made of such a material as will enable diffusion of only the dissolved gases in the fluid passed through the pipe line into the electrolyte chamber 9, and the central portion of the member 21 is reduced in diameter to provide a thin-walled section functioning as the membrane 3. This central thin-walled portion is also provided with a series of parallel spaced circumferentially extending ribs establishing grooves therebetween, the complete surfaces of the ribs and grooves being covered with a layer of cathode material. The interior wall of sheath 10 is likewise provided with a series of parallel spaced circumferentially placed ribs establishing grooves therebetween, the complete surfaces of the ribs and grooves being covered with a layer of anode material.

Figure 4:
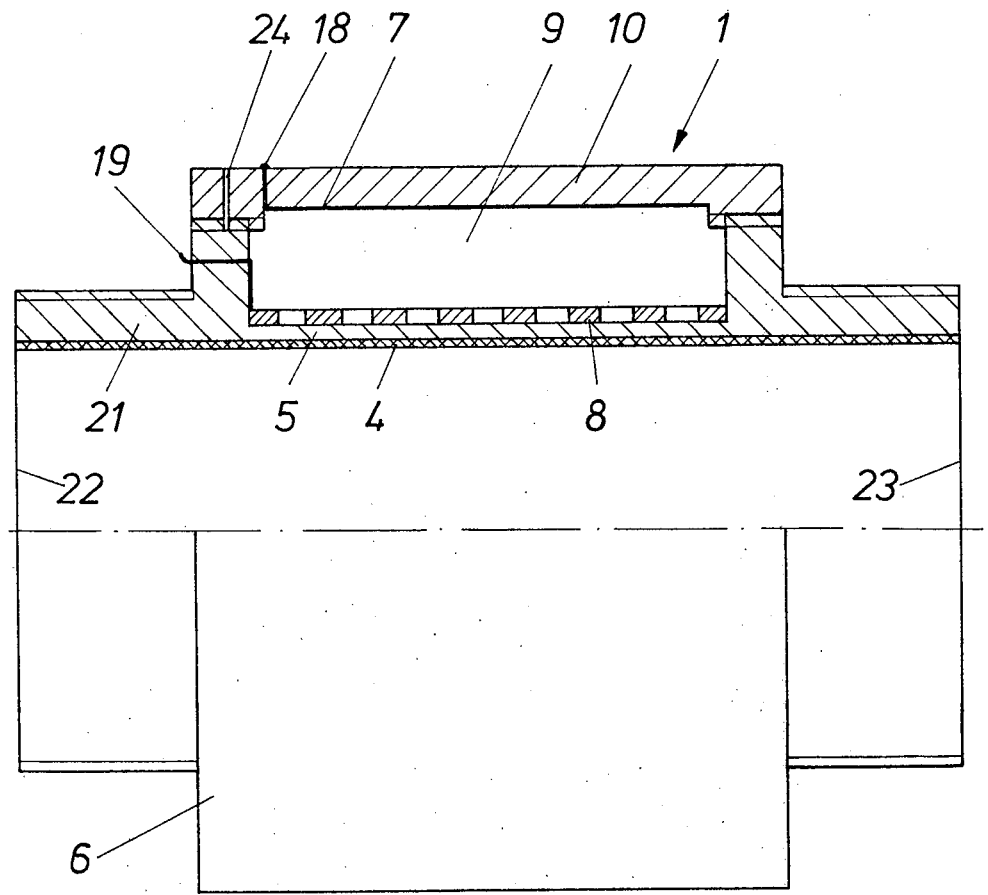

In the embodiment of FIG. 4, the tubular member 21 includes a gas-permeable central thin-walled section 5 which serves as the membrane and also a back-up support for the complete surface of a gas diffusion-controlling layer 4 applied to the inner surface of tubular member 21. A cathode 8 in the form of a perforated sheet metal tube is applied to the radially outer surface of the thin-walled part of the gas-permeable tubular member 21 and an anode 7 in the form of a layer of suitable material is applied to the inner surface of sheath 10. The latter is fastened in place by means of screws in such manner that an aperture 24 for filing the electrolyte chamber 9 is unobstructed when the sheath is only partially screwed on but is closed tightly when the sheath is screwed completely into place onto the flanged portions of the tubular member 21.

Figure 5:
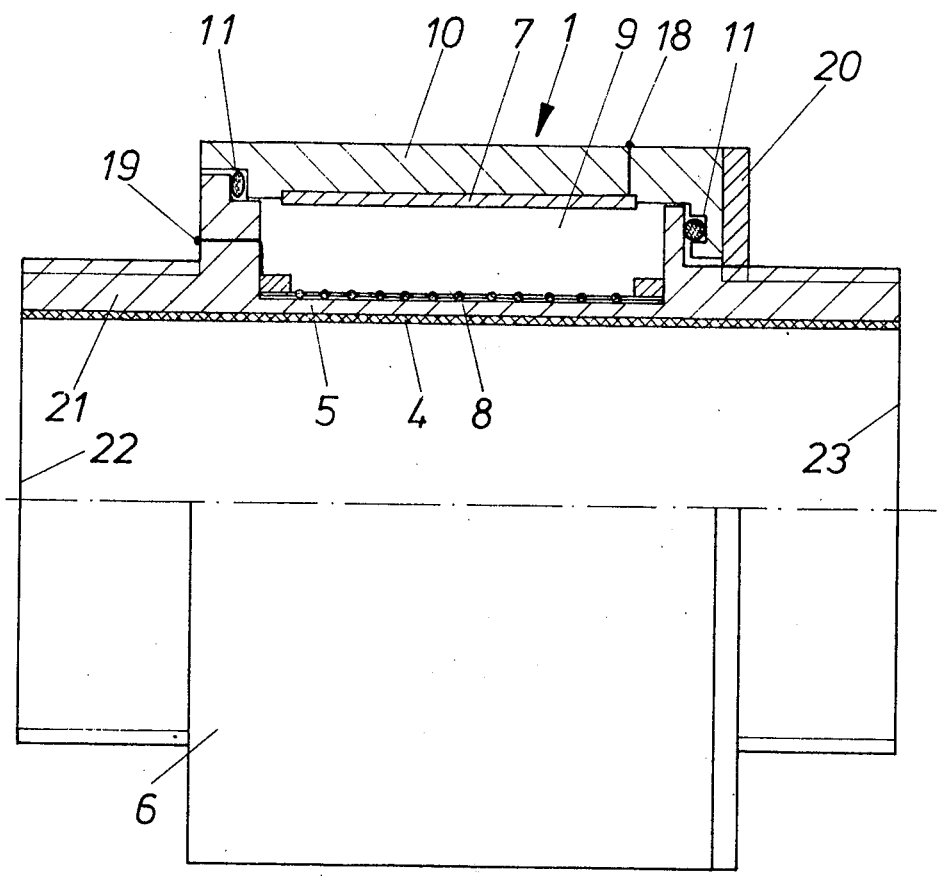

The embodiment of FIG. 5 is similar to that of FIG. 4 except with respect to the physical structures of the electrodes, the cathode 8 being in the form of a cylindrical wire mesh and the anode 7 being in the form of a metallic tubular member applied to the inner face of the sheath 10. Also, minor differences exist with respect to the manner in which the sheath 10 is applied, a shouldered fit being provided which includes engaged shouldered portions and seal ring 11 at one end of sheath 10 and similar shouldered portions and sealing ring 11 at the opposite end of sheath 10, the fastening of the sheath in place on the tubular member 21 being effected by means of a longitudinal displacement between the two accomplished by a threaded ring 20.

Figure 6:
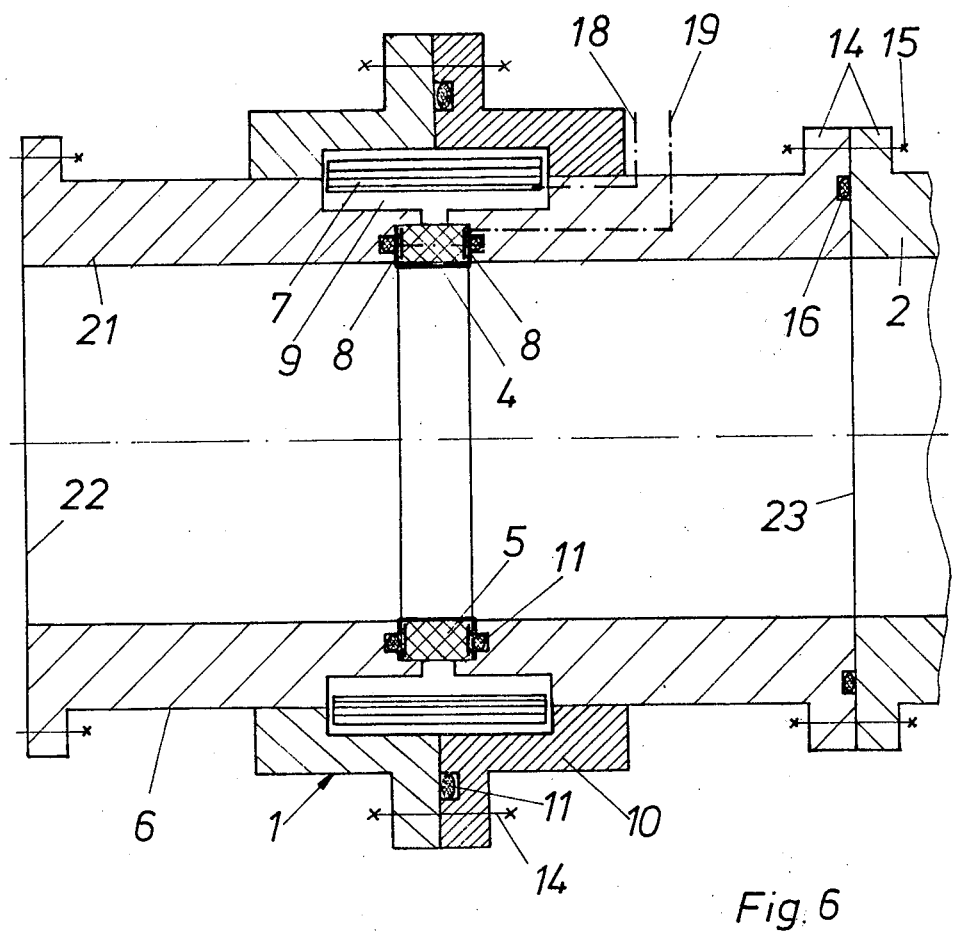

In FIG. 6, the central portion of the tubular member 21 is provided with a circumferentially extending groove within which is seated a gas-permeable support ring 5 and to the inner periphery of which is applied the membrane 4. The base of the groove leads into the electrolyte chamber 9 within which the anode 7 is located, and the cathode 8 is provided in the form of two rings applied to the opposite faces of the support ring 5. Sheath 10 is made in two halves including connection flanges 14 therefor.

Figure 7:
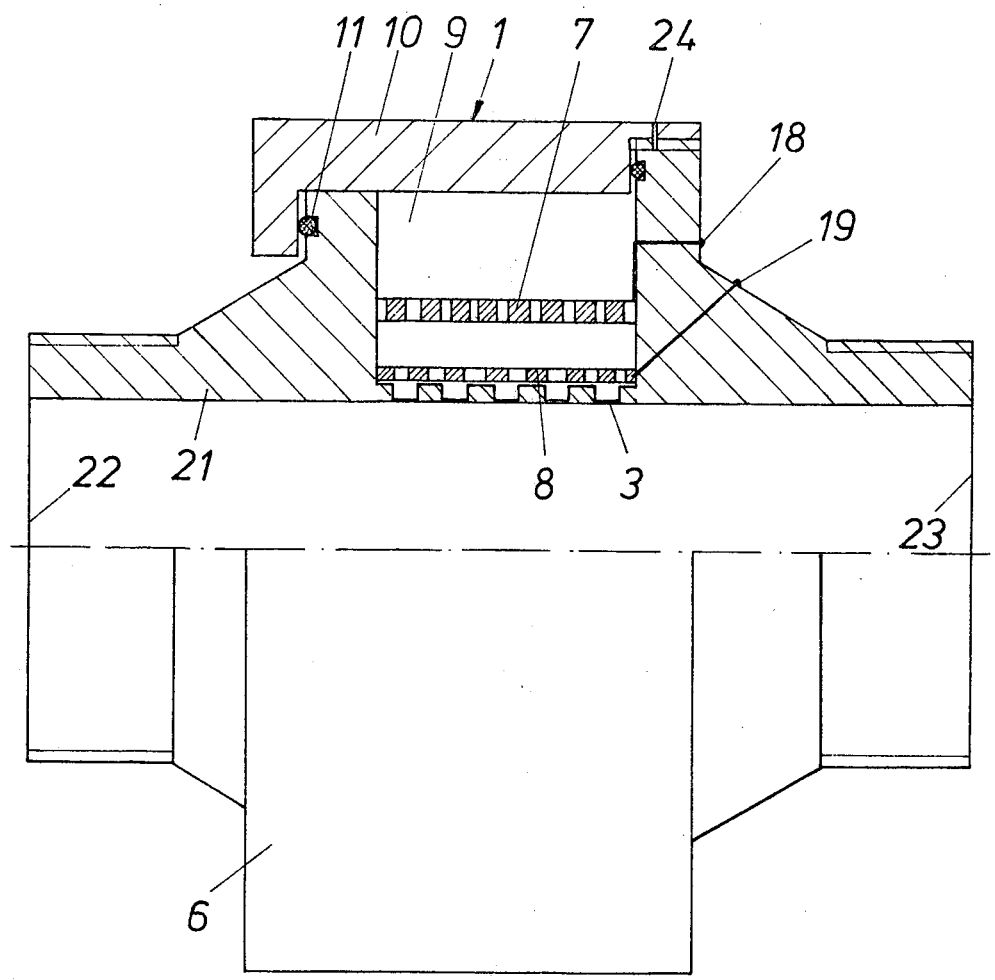

The embodiment of FIG. 7 is similar to that of FIG. 5 so far as concerns the sheath 10, and the tubular member 21 includes a central thin-walled portion which functions as the membrane 3. The cathode 8 and anode 7 are both in the form of cylindrical foraminated material.

Figure 8:
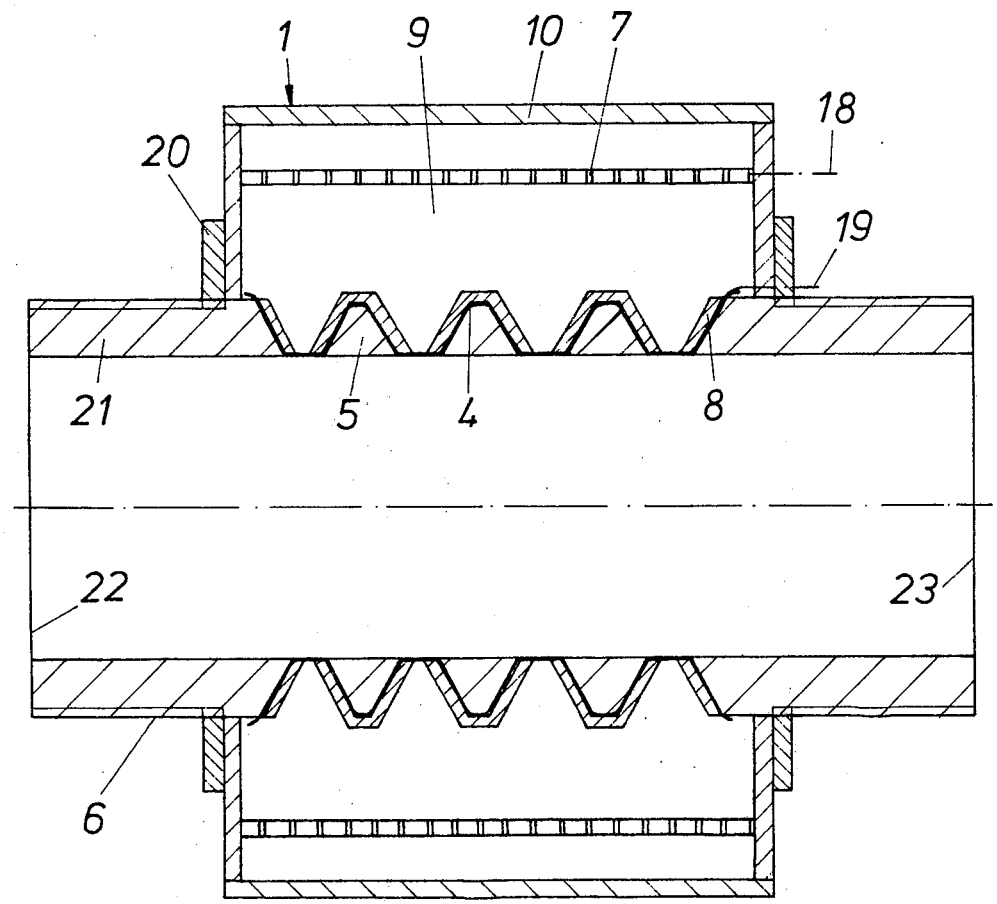

In FIG. 8 the tubular member 21 includes a gas-permeable central supporting portion 5 for the membrane 4, the cathode 8 being applied directly to the surface of the membrane and the anode 7 being in the form of a cylindrical foraminated member.

Figure 9:
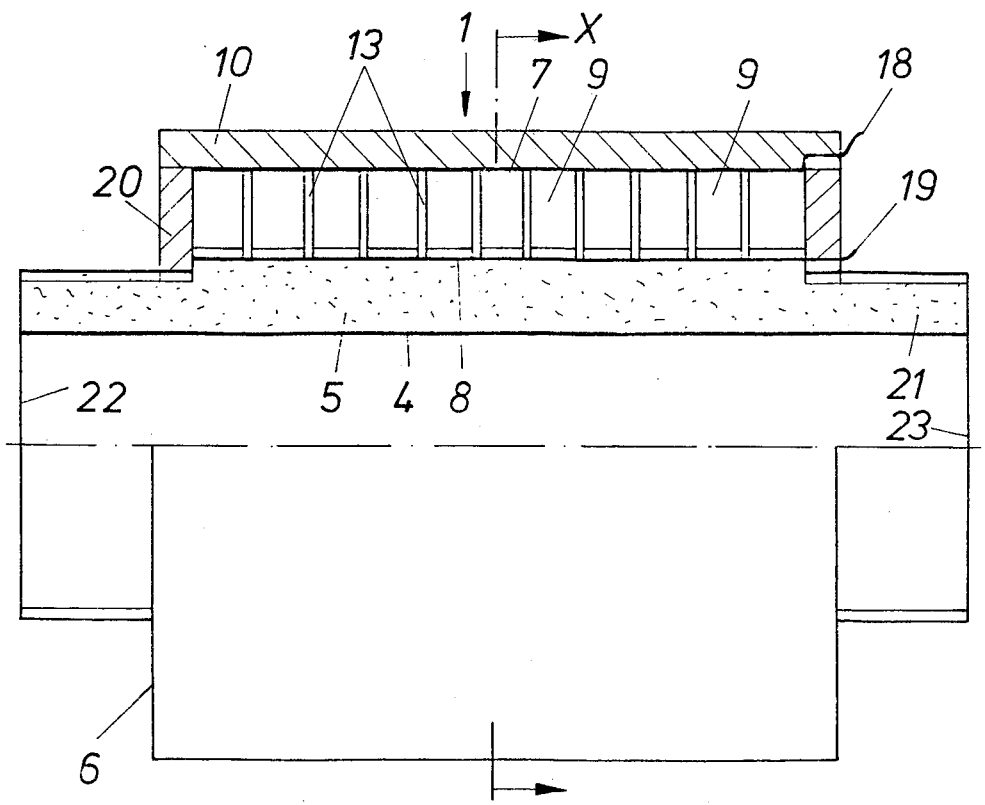
Figure 10:
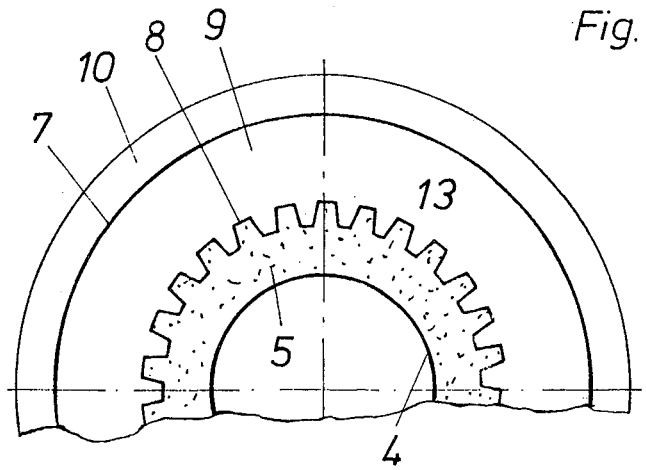

In the embodiment shown in FIGS. 9 and 10, a supporting part 5 of the tubular member 21 has the membrane 4 applied to the inner surface thereof and the outer surface thereof carries the cathode 8. The anode 7 is applied to the inner surface of sheath 10 and the electrolyte chamber 9 is divided into a series of axially spaced part-chambers by means of a series of axially spaced annular separating walls 13. This supporting part 5 is made of ceramic and is permeable to the dissolved gas, e.g. $O_2$. As shown in FIG. 10, the membrane supporting part 5 is ribbed in the axial direction to facilitate the $O_2$ diffusion. The parallel connection is accomplished in this case by the electrodes which are continuous in an axial direction through all of the part-chambers 9. However, the electrodes can also be arranged separately, for example, at the separating walls 13, and with suitable electrical lead-outs which are then interconnected electrically.

We claim:

1. Apparatus for polarographically measuring dissolved gases in a liquid which comprises a cylindrical pipe line through which the liquid to be measured is flowed, a cylindrical polarographic measuring cell in said pipe line, said cell comprising a cylindrical tubular member which includes a wall portion intermediate the ends thereof made of a material enabling the dissolved gases in the liquid to diffuse therethrough but being impermeable with respect to the liquid, means including a sheath surrounding said gas-diffusible intermediate wall portion of said tubular member in radial spaced relation to establish an annular electrolyte-filled chamber, a cathode structure applied to the outer periphery of said gas-diffusible intermediate wall portion and which extends throughout the entire circumference thereof, a circumferentially extending anode structure located radially outward from said cathode structure and a circumferentially extending support for said anode located intermediate said cathode and anode and which is permeable to the electrolyte.

2. Apparatus for polarographically measuring dissolved gases in a liquid which comprises a cylindrical pipe line through which the liquid to be measured is flowed, a cylindrical polarographic measuring cell in said pipe line, said cell comprising a cylindrical tubular member which includes a wall portion intermediate the ends thereof made of a material enabling the dissolved gases in the liquid to diffuse therethrough but being impermeable with respect to the liquid, means including a sheath surrounding said gas-diffusible intermediate wall portion of said tubular member in radial spaced relation to establish an annular electrolyte-filled chamber, radially spaced and circumferentially extending cathode and anode elements supported within said electrolyte chamber, and wall means subdividing said electrolyte chamber into a plurality of individual chambers and with their respective cathode and anodes connected electrically in 3. A polarographic measuring apparatus as defined in claim 2 wherein said wall means which divide said annular electrolyte chamber into a plurality of individual chambers are constituted by radially extending and parallel spaced annular walls surrounding said gas-diffusible intermediate wall portion of said tubular member.

4. Apparatus for polarographically measuring dissolved gases in a liquid which comprises a cylindrical pipe line through which the liquid to be measured is flowed, a cylindrical polarographic measuring cell in said pipe line, said cell comprising a cylindrical tubular member which includes a wall portion intermediate the ends thereof made of a material enabling the dissolved gases in the liquid to diffuse therethrough but being impermeable with respect to the liquid, means including a sheath surrounding said gas-diffusible intermediate wall portion of said tubular member in radial spaced relation to establish an annular electrolyte-filled chamber, the outer periphery of said gas-diffusible intermediate wall portion of said tubular member having a rib-like configuration, a cathode structure applied to the surface of said rib-like periphery throughout the entire circumference thereof, and a circumferentially extending anode structure located radially outward from and completely surrounding said rib-like cathode structure.

5. Apparatus for polarographically measuring dissolved gases in a liquid which comprises a cylindrical pipe line through which the liquid to be measured is flowed, a cylindrical polargraphic measuring cell in said pipe line, said said cell comprising a cylindrical tubular member which includes a wall portion intermediate the ends thereof made of a material enabling the dissolved gases in the liquid to diffuse therethrough but being impermeable with respect to the liquid, means including a sheath surrounding said gas-diffusible intermediate wall portion of said tubular member in radial spaced relation to establish an annular electrolyte-filled chamber, a cathode structure applied to the outer periphery of said gas-diffusible intermediate wall portion and which extends throughout the entire circumference thereof, the inner periphery of said sheath having a rib-like configuration and an anode structure applied to the surface of said rib-like periphery of said sheath throughout the entire circumference thereof.

6. Apparatus for polarographically measuring dissolved gases in a liquid which comprises a cylindrical pipe line through which the liquid to be measured is flowed, a cylindrical polarographic measuring cell in said pipe line, said cell comprising a cylindrical tubular member which includes a wall portion intermediate the ends thereof made of a material enabling the dissolved gases in the liquid to diffuse therethrough but being impermeable with respect to the liquid, means including a sheath surrounding said gas-diffusible intermediate wall portion of said tubular member in radial spaced relation to establish an annular electrolyte-filled chamber, said gas-diffisible intermediate wall portion of said tubular member including a gas-permeable cathode support ring seated in a circumferentially extending groove therein and which communicates with said electrolyte chamber, a cathode structure constituted by two rings applied respectively to opposite faces of said support ring and a circumferentially extending anode structure located radially outward from said cathode rings in said electrolyte chamber.

* * * * *

UNITED STATES PATENT OFFICE
CERTIFICATE OF CORRECTION

PATENT NO. : 3,988,233
DATED : October 26, 1976
INVENTOR(S) : Gerold Gamer, et al It is certified that error appears in the above-identified patent and that said Letters Patent are hereby corrected as shown below:

In claim 2, at the end of the claim after "in"

insert - parallel -

In claim 5, line 5 cancel one of the "said" before "cell"

In claim 6, line 15, spell "diffusible" thus .

Signed and Sealed this

Twenty-first Day of December 1976

[SEAL]

Attest:

RUTH C. MASON
*Attesting Officer*

C. MARSHALL DANN
*Commissioner of Patents and Trademarks*